United States Patent
Okawa et al.

(10) Patent No.: US 9,598,576 B2
(45) Date of Patent: Mar. 21, 2017

(54) CURABLE SILICONE COMPOSITION, CURED PRODUCT THEREOF, AND OPTICAL SEMICONDUCTOR DEVICE

(71) Applicants: Dow Corning Toray Co., Ltd., Tokyo (JP); Dow Corning Corporation, Midland, MI (US)

(72) Inventors: Tadashi Okawa, Ichihara (JP); Tomohiro Iimura, Ichihara (JP); Sawako Inagaki, Ichihara (JP); Mayumi Mizukami, Ichihara (JP); Michitaka Suto, Ichihara (JP); Haruhiko Furukawa, Ichihara (JP); Randall G. Schmidt, Midland, MI (US); Adam C. Tomasik, Mount Pleasant, MI (US)

(73) Assignees: DOW CORNING TORAY CO., LTD., Chiyoda-Ku, Tokyo (JP); DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 14/915,824

(22) PCT Filed: Sep. 3, 2014

(86) PCT No.: PCT/JP2014/073249
§ 371 (c)(1),
(2) Date: Mar. 1, 2016

(87) PCT Pub. No.: WO2015/033979
PCT Pub. Date: Mar. 12, 2015

(65) Prior Publication Data
US 2016/0194496 A1 Jul. 7, 2016

Related U.S. Application Data

(60) Provisional application No. 61/873,160, filed on Sep. 3, 2013.

(51) Int. Cl.
*C08L 83/04* (2006.01)
*C08K 5/00* (2006.01)
(Continued)

(52) U.S. Cl.
CPC ............ *C08L 83/04* (2013.01); *C07F 7/0859* (2013.01); *C07F 7/0872* (2013.01);
(Continued)

(58) Field of Classification Search
None
See application file for complete search history.

(56) References Cited

U.S. PATENT DOCUMENTS 2,445,567 A 7/1948 Elliott
3,002,989 A 10/1961 Awe et al.
(Continued)

FOREIGN PATENT DOCUMENTS

EP 0 231 519 A2 8/1987
EP 0 335 344 A2 10/1989
(Continued)

OTHER PUBLICATIONS

International Search Report for Application No. PCT/JP2014/073249 dated Dec. 16, 2014, 5 pages.
(Continued)

*Primary Examiner* — Robert S Loewe
(74) *Attorney, Agent, or Firm* — Howard & Howard Attorneys PLLC (57) ABSTRACT

The present invention relates to a curable silicone composition comprising: (A) an organopolysiloxane having at least two alkenyl groups and at least one aryl group in a molecule, (B) an organopolysiloxane having at least two silicon atom-bonded hydrogen atoms in a molecule, (C) an organopolysiloxane having at least one aryl group in a molecule and containing a metal atom selected from the group consisting
(Continued)

of V, Ta, Nb and Ce, and (D) a hydrosilylation-reaction catalyst. The present invention can provide the curable silicone composition, which does not develop a crack by thermal aging and further can form a cured material that exhibits less yellowing.

16 Claims, 3 Drawing Sheets

(51) Int. Cl.
| | |
|---|---|
| *C07F 7/08* | (2006.01) |
| *C08K 5/5419* | (2006.01) |
| *C09D 183/04* | (2006.01) |
| *C09J 183/04* | (2006.01) |
| *C09K 11/08* | (2006.01) |
| *C09K 11/64* | (2006.01) |
| *H01L 33/56* | (2010.01) |

(52) U.S. Cl.
CPC .......... *C08K 5/0091* (2013.01); *C08K 5/5419* (2013.01); *C09D 183/04* (2013.01); *C09J 183/04* (2013.01); *C09K 11/0883* (2013.01); *C09K 11/641* (2013.01); *H01L 33/56* (2013.01); *H01L 2224/48091* (2013.01); *H01L 2224/48247* (2013.01); *H01L 2924/181* (2013.01)

(56) References Cited

U.S. PATENT DOCUMENTS

| | | | | |
|---|---|---|---|---|
| 3,008,901 | A * | 11/1961 | Baker | C08K 3/22 508/209 |
| 3,267,036 | A * | 8/1966 | Baker | C08G 77/398 508/201 |
| 3,377,312 | A | 4/1968 | Baney et al. | |
| 3,865,784 | A | 2/1975 | Neale et al. | |
| 3,884,950 | A | 5/1975 | Koda et al. | |
| 3,912,831 | A * | 10/1975 | Kan | B41M 5/136 427/150 |
| RE28,938 | E * | 8/1976 | Koda | C08K 5/5406 508/201 |
| 4,070,343 | A * | 1/1978 | Kishimoto | C08K 5/057 508/201 |
| 4,334,051 | A * | 6/1982 | Yajima | C08G 77/58 525/474 |
| 4,358,576 | A * | 11/1982 | Yajima | C08G 77/58 528/25 |
| 4,361,679 | A * | 11/1982 | Yajima | C08G 77/56 525/389 |
| 4,361,691 | A * | 11/1982 | Yajima | C08G 77/54 525/475 |
| 4,379,094 | A | 4/1983 | DiSalvo et al. | |
| 4,560,784 | A * | 12/1985 | Mori | C08G 77/398 556/401 |
| 4,663,439 | A | 5/1987 | Gradeff et al. | |
| 4,722,957 | A * | 2/1988 | Braun | C08G 77/398 524/262 |
| 4,898,956 | A * | 2/1990 | Hilty | C07F 7/0836 556/401 |
| 4,948,826 | A * | 8/1990 | Hirai | C08K 5/5406 524/306 |
| 5,017,694 | A | 5/1991 | Gradeff et al. | |
| 5,017,695 | A * | 5/1991 | Gradeff | C03C 1/00 534/15 |
| 5,391,638 | A * | 2/1995 | Katsoulis | C08G 79/14 525/389 |
| 6,043,309 | A * | 3/2000 | Nakamura | C08K 5/5419 524/106 |
| 6,045,961 | A * | 4/2000 | Heeks | G03G 15/2025 399/325 |
| 6,284,829 | B1 * | 9/2001 | Dalbe | C08K 3/22 524/430 |
| 8,029,904 | B2 | 10/2011 | Mosley et al. | |
| 8,129,480 | B2 | 3/2012 | Takanashi et al. | |
| 8,142,895 | B2 | 3/2012 | Khanarian et al. | |
| 8,404,877 | B2 * | 3/2013 | Kniajanski | C07F 7/0836 428/447 |
| 2004/0022978 | A1 * | 2/2004 | Fehn | A23G 1/226 428/35.7 |
| 2006/0073347 | A1 * | 4/2006 | Morita | C08L 83/04 428/447 |
| 2008/0139695 | A1 * | 6/2008 | Dubouis | C08K 3/0008 523/173 |
| 2008/0255304 | A1 * | 10/2008 | Nakashima | C08L 83/04 525/100 |
| 2008/0255321 | A1 * | 10/2008 | Nakashima | B32B 25/20 525/476 |
| 2011/0077344 | A1 * | 3/2011 | Hasegawa | C08L 83/04 524/500 |
| 2012/0065308 | A1 | 3/2012 | Sumi et al. | |
| 2013/0161686 | A1 * | 6/2013 | Yoshitake | H01L 24/29 257/100 |
| 2014/0235806 | A1 * | 8/2014 | Miyamoto | C08L 83/04 526/126 |
| 2015/0376344 | A1 | 12/2015 | Dent et al. | |

FOREIGN PATENT DOCUMENTS

| | | |
|---|---|---|
| EP | 0 426 578 A1 | 5/1991 |
| EP | 0 699 717 A2 | 3/1996 |
| FR | 2 654 110 A1 | 5/1991 |
| GB | 1 393 078 | 5/1975 |
| JP | S 49-83744 A | 8/1974 |
| JP | S 51-041046 A | 4/1976 |
| JP | S 60-240761 A | 11/1985 |
| JP | S 62-256863 A | 11/1987 |
| JP | H 01-247462 A | 10/1989 |
| JP | H 03-168250 A | 7/1991 |
| JP | H 10-231428 A | 9/1998 |
| JP | 2006-008771 A | 1/2006 |
| JP | 2006-335857 A | 12/2006 |
| WO | WO 2006/001458 A2 | 1/2006 |
| WO | WO 2008/047892 A1 | 4/2008 |
| WO | WO 2013/192404 A1 | 12/2013 |
| WO | WO 2013/192419 A1 | 12/2013 |

OTHER PUBLICATIONS

International Search Report for Application No. PCT/US2014/053696 dated Nov. 27, 2014, 3 pages.
Bradley et al., "Organosilyloxy-Derivatives of Metals. Part I. Alkylsilyloxy-Derivatives of Titanium, Zirconium, Niobium, and Tantalum", Journal of the Chemical Society (Royal Society), 1959, pp. 3404-3411.
U.S. Appl. No. 61/873,081, filed Sep. 3, 2013.
English language abstract and machine-assisted English translation for EP 0 426 578 extracted from espacenet.com database on Apr. 18, 2016, 12 pages.
Machine-assisted English translation for FR 2 654 110 extracted from espacenet.com database on Apr. 18, 2016, 23 pages.
English language abstract not found for JPS 49-83744; however, see English language equivalent GB 1 393 078. Original document extracted from espacenet.com on Apr. 18, 2016, 5 pages.
Machine-assisted English translation for JPS 51-041046 extracted from the PAJ database on Apr. 18, 2016, 4 pages.
English language abstract and machine-assisted English translation for JPS 60-240761 extracted from the PAJ database on Apr. 18, 2016, 8 pages.
English language abstract and machine-assisted English translation for JPS 62-256863 extracted from the PAJ database on Apr. 18, 2016, 11 pages.
English language abstract for JPH 01-247462 extracted from espacenet.com database on Apr. 18, 2016, 2 pages.
English language abstract and machine-assisted English translation for JPH 03-168250 extracted from espacenet.com database on Apr. 18, 2016, 17 pages.

(56) References Cited

OTHER PUBLICATIONS

English language abstract and machine-assisted English translation for JPH 10-231428 extracted from espacenet.com database on Apr. 18, 2016, 15 pages.
English language abstract for JP 2006-008771 extracted from espacenet.com database on Apr. 18, 2016, 2 pages.
English language abstract and machine-assisted English translation for JP 2006-335857 extracted from espacenet.com database on Apr. 18, 2016, 16 pages.
English language abstract for WO 2008/047892 extracted from espacenet.com database on Apr. 18, 2016, 2 pages.

* cited by examiner

CURABLE SILICONE COMPOSITION, CURED PRODUCT THEREOF, AND OPTICAL SEMICONDUCTOR DEVICE

RELATED APPLICATIONS

This application is the National Stage of International Patent Application No. PCT/JP2014/073249, filed on Sep. 3, 2014, which claims priority to and all the advantages of U.S. Provisional Patent Application No. 61/873,160, filed on Sep. 3, 2013, the content of which is incorporated herein by reference.

TECHNICAL FIELD

The present invention relates to a curable silicone composition, a cured product thereof, and an optical semiconductor device fabricated using the composition.

BACKGROUND ART

A curable silicone composition, which can be cured by a hydrosilylation reaction, is used for various applications because it forms a cured product having excellent rubber characteristics such as hardness and elongation. Known examples of curable silicone compositions include: a curable silicone composition including: a straight-chain organopolysiloxane having at least two alkenyl groups in a molecule; an organopolysiloxane comprising $SiO_{4/2}$ units, $ViR_2SiO_{1/2}$ units, and $R_3SiO_{1/2}$ units, where Vi is a vinyl group, and R is a substituted or unsubstituted monovalent hydrocarbon group having no unsaturated aliphatic bond; an organopolysiloxane having at least one silicon-bonded alkoxy group and at least two silicon-bonded hydrogen atoms in a molecule; and a platinum metal-based catalyst (see Patent Document 1) and a curable silicone composition including: a straight-chain organopolysiloxane having at least two alkenyl groups in a molecule; an organopolysiloxane comprising $SiO_{4/2}$ units and $R'(CH_3)_2SiO_{1/2}$ units, where R' is either an alkenyl group or a methyl group, and having at least three alkenyl groups in a molecule; an organopolysiloxane comprising $SiO_{4/2}$ units and $R''(CH_3)_2SiO_{1/2}$ units, where R" is either a hydrogen atom or a methyl group, and having at least three silicon-bonded hydrogen atoms in a molecule; and a platinum group metal compound (see Patent Documents 2 and 3).

These curable silicone compositions are suitable as a sealing agent for an optical semiconductor device, producing no byproducts and forming transparent cured materials. However, there is a problem of crack formation in the cured product, leading to degradation in adhesion and sealing performance with a substrate, and a decrease in transparency, when used in the environment with the temperature not less than 200° C. for a long duration.

Meanwhile, it is known that the addition of an organopolysiloxane containing cerium to a curable silicone composition improves the heat resistance thereof (e.g. see Patent Documents 4 and 5). However, the organopolysiloxane containing cerium exhibits yellow color and has never been used as a curable silicone composition for an optical semiconductor device, where transparency is required.

CITATION LIST

Patent Literature

Patent Literature 1: Japanese Unexamined Patent Application Publication No. H10-231428A
Patent Literature 2: Japanese Unexamined Patent Application Publication No. 2006-335857A
Patent Literature 3: WO2008/047892 pamphlet
Patent Literature 4: Japanese Unexamined Patent Application Publication No. S49-83744A
Patent Literature 5: Japanese Unexamined Patent Application Publication No. S51-41046A

SUMMARY OF INVENTION

Technical Problem

An object of the present invention is to provide a curable silicone composition, which does not develop a crack by thermal aging and further can form a cured material that exhibits less yellowing. Also, another objective of the present invention is to provide a cured product which does not form a crack by thermal aging and exhibits less yellowing; and further to provide an optical semiconductor device, in which the coloring of a lead frame is less, thus being excellent in reliability.

Solution to Problem

The curable silicone composition of the present invention comprises:

(A) an organopolysiloxane having at least two alkenyl groups and at least one aryl group in a molecule;

(B) an organopolysiloxane having at least two silicon-bonded hydrogen atoms in a molecule, in an amount such that the silicon-bonded hydrogen atoms in component (B) is from 0.1 to 10 moles per 1 mole of the alkenyl groups in component (A);

(C) an organopolysiloxane having at least one aryl group in a molecule and a metal atom selected from the group consisting of V, Ta, Nb, and Ce, in an amount such that the metal atom in component (C) is from 20 to 2,000 ppm in terms of mass units based on the content of the present composition; and (D) a catalytic amount of hydrosilylation reaction catalyst.

The curable silicone composition is preferable, wherein component (A) is a mixture comprising: (A-1) a straight-chain organopolysiloxane having at least two alkenyl groups and at least one aryl group in a molecule; and (A-2) an organopolysiloxane represented by the following average unit formula:

$(R^1SiO_{3/2})_a(R^1{}_2SiO_{2/2})_b(R^1{}_3SiO_{1/2})_c(SiO_{4/2})_d(XO_{1/2})_e$ wherein $R^1$ is each independently an alkyl group having from 1 to 12 carbons, an alkenyl group having from 2 to 12 carbons, an aryl group having from 6 to 20 carbons, an aralkyl group having from 7 to 20 carbons, or a group with halogen atoms substituting a portion of or all of hydrogen atoms thereof; at least two $R^1$ in a molecule are the alkenyl groups; X is a hydrogen atom or an alkyl group; and "a" is a number of 0 to 0.3, "b" is 0 or a positive number, "c" is a positive number, "d" is a positive number, and "e" is a number of 0 to 0.4, and they satisfy: a+b+c+d=1, c/d is a number of 0 to 10 and b/d is a number of 0 to 0.5; in an amount such that a mass ratio of component (A-1) to component (A-2) is from 1/99 to 99/1.

The curable silicone composition is preferable, wherein component (A-2) includes: an alkenyl group having from 2 to 12 carbons in an amount from 0.1 to 40 mol % of the total amount of $R^1$; and an alkyl group having from 1 to 12 carbons in an amount not less than 10 mol % of the total amount of $R^1$.

The curable silicone composition is preferable, wherein component (A-2) is an organopolysiloxane including: $R^1(CH_3)_2SiO_{1/2}$ units and $SiO_{4/2}$ units, wherein $R^1$ is an alkyl group having from 1 to 12 carbons, an alkenyl group having from 2 to 12 carbons, an aryl group having from 6 to 20 carbons, an aralkyl group having from 7 to 20 carbons, or a group with halogen atoms substituting a portion of or all of hydrogen atoms thereof and at least two of $R^1$ in a molecule are the alkenyl groups.

The present composition can further include (E) a hydrosilylation reaction inhibitor, in an amount from 0.01 to 3 parts by mass per 100 parts by mass of the total of components (A) to (C).

The present composition can further include (F) an adhesion promoter, in an amount from 0.1 to 3 parts by mass per 100 parts by mass of the total of components (A) to (C).

The present composition can further include (G) a fluorescent substance, in an amount from 0.1 to 70 mass % of the present composition.

Furthermore, the present composition preferably has an optical transmittance not less than 90% at 450 nm.

Furthermore, the present composition preferably forms a cured product having a value of b* in the CIE L*a*b* color space defined in JIS Z 8730 not more than 2.0, before and after being heated at 240° C. for 500 hours.

The cured product of the present invention is formed by curing the curable silicone composition described above.

The optical semiconductor device of the present invention is fabricated by sealing, coating, or adhering an optical semiconductor element, using the curable silicone composition described above.

Also, the optical semiconductor element may be a light emitting diode.

Advantageous Effects of Invention

The curable silicone composition of the present invention is characterized by the ability to form a cured product, which does not develop a crack by thermal aging and exhibits less yellowing. The cured product of the present invention also does not develop a crack by thermal aging and exhibits less yellowing. Furthermore, the optical semiconductor device of the present invention includes a cured product for sealing, covering or adhering a semiconductor element developing few cracks, and has an excellent reliability. Especially, the optical semiconductor device using silver for a lead frame or a reflective member is characterized by little coloring of the silver.

DESCRIPTION OF EMBODIMENTS

[Curable Silicone Composition]

First, the curable silicone composition of the present invention will be described in detail.

Component (A) is an organopolysiloxane, which has at least two alkenyl groups and at least one aryl group in a molecule. Examples of the alkenyl groups in component (A) include alkenyl groups having from 2 to 12 carbons, such as a vinyl group, an allyl group, a butenyl group, a pentenyl group, a hexenyl group, a heptenyl group, an octenyl group, a nonenyl group, a decenyl group, an undecenyl group and a dodecenyl group. The vinyl group is preferable. Examples of the aryl groups in component (A) include aryl groups having from 6 to 20 carbons, such as a phenyl group, a tolyl group, a xylyl group, and a naphthyl group. The phenyl group is preferable. Also, examples of the groups that bond to silicon atoms other than the alkenyl groups and the aryl groups in component (A) include: alkyl groups having from 1 to 12 carbons, such as a methyl group, an ethyl group, a propyl group, an isopropyl group, an n-butyl group, an isobutyl group, a tert-butyl group, an n-pentyl group, a neopentyl group, a hexyl group, a cyclohexyl group, a heptyl group, an octyl group, a nonyl group, a decyl group, an undecyl group, and a dodecyl group; aralkyl groups having from 7 to 20 carbons, such as a benzyl group, a phenethyl group, and a phenylpropyl group; and groups with halogen atoms, such as fluorine atoms, chlorine atoms and bromine atoms, substituting a portion of or all of the hydrogen atoms of these groups. Meanwhile, the silicon atoms in component (A) may bond a small amount of hydroxyl groups and alkoxy groups such as methoxy groups and ethoxy groups without departing from the scope of the present invention.

A molecular structure of component (A) is not particularly limited and the examples thereof include straight-chain, partially branched straight, branched chain, and dendritic. Component (A) may be a mixture of two or more types of organopolysiloxanes having these molecular structures.

The curable silicone composition is preferable, wherein component (A) is a mixture comprising (A-1) a straight-chain organopolysiloxane having at least two alkenyl groups and at least one aryl group in a molecule; and (A-2) an organopolysiloxane represented by the following average unit formula:

$(R^1SiO_{3/2})_a(R^1{}_2SiO_{2/2})_b(R^1{}_3SiO_{1/2})_c(SiO_{4/2})_d(XO_{1/2})_e.$

A viscosity at 25° C. of component (A-1) is not limited, but is preferably in a range of 10 to 1,000,000 mPa·s and more preferably in a range of 50 to 100,000 mPa·s. When the viscosity of component (A-1) is greater than or equal to the minimum value of the range given above, mechanical strength of the cured product obtained is good, while when it is less than or equal to the maximum value of the range given above, handling and processability of the composition obtained is good.

Examples of component (A-1) include: a dimethylpolysiloxane terminated with methylphenylvinylsiloxy groups at both molecular terminals, a dimethylpolysiloxane terminated with diphenylvinylsiloxy groups at both molecular terminals, a dimethylsiloxane-methylphenylsiloxane copolymer terminated with dimethylvinylsiloxy groups at both molecular terminals, a dimethylsiloxane-diphenylsiloxane copolymer terminated with dimethylvinylsiloxy groups at both molecular terminals, a methylphenylsiloxane terminated with dimethylvinylsiloxy groups at both molecular terminals, a methylphenylsiloxane-diphenylsiloxane copolymer terminated with dimethylvinylsiloxy groups at both molecular terminals, a dimethylsiloxane-methylphenylsiloxane copolymer terminated with methylphenylvinylsiloxy groups at both molecular terminals, a dimethylsiloxane-methylphenylsiloxane copolymer terminated with diphenylvinylsiloxy groups at both molecular terminals, a methylphenylsiloxane terminated with methylphenylvinylsiloxy groups at both molecular terminals, a methylphenylsiloxane-diphenylsiloxan copolymer terminated with methylphenylvinylsiloxy groups at both molecular terminals, a dimethylsiloxane-methylphenylsiloxane copolymer terminated with diphenylvinylsiloxy groups at both molecular terminals, a phenylmethylsiloxane terminated with diphenylvinylsiloxy groups at both molecular terminals, a phenylmethylsiloxane-diphenylsiloxane copolymer terminated with diphenylvinylsiloxy groups at both molecular terminals, a dimethylsiloxane-methylphenylsiloxane-methylvinylsiloxane copolymer terminated with dimethylvinylsiloxy groups at both molecular terminals, a dimethylsiloxane-diphenylsiloxane-methylvinylsiloxane copolymer terminated with dimethylvinylsiloxy groups at both molecular terminals, a methylvinylpolysiloxane terminated with trimethylsiloxy groups at both molecular terminals, a methylvinylsiloxane-methylphenylsiloxane copolymer terminated with trimethylsiloxy groups at both molecular terminals, a methylvinylsiloxane-diphenylsiloxane copolymer terminated with trimethylsiloxy groups at both molecular terminals, and a dimethylsiloxane-methylvinylsiloxane copolymer terminated with trimethylsiloxy groups at both molecular terminals.

In the formula for component (A-2), $R^1$ is each independently an alkyl group having from 1 to 12 carbons, an alkenyl group having from 2 to 12 carbons, an aryl group having from 6 to 20 carbons, an aralkyl group having from 7 to 20 carbons, or a group having halogen atoms substituting a portion of or all of the hydrogen atoms of these groups. Examples of the alkyl group of $R^1$ include a methyl group, an ethyl group, a propyl group, an isopropyl group, an n-butyl group, an isobutyl group, a tert-butyl group, an n-pentyl group, a neopentyl group, a hexyl group, a cyclohexyl group, a heptyl group, an octyl group, a nonyl group, a decyl group, an undecyl group, and a dodecyl group. Examples of the alkenyl groups of $R^1$ include a vinyl group, an allyl group, a butenyl group, a pentenyl group, a hexenyl group, a heptenyl group, an octenyl group, a nonenyl group, a decenyl group, an undecenyl group, and a dodecenyl group. Examples of the aryl groups in $R^1$ include a phenyl group, a tolyl group, a xylyl group, and a naphthyl group. Examples of the aralkyl groups in $R^1$ include a benzyl group, a phenethyl group, and a phenylpropyl group. Examples of the halogen-substituted groups in $R^1$ include a 3-chloropropyl group, and a 3,3,3-trifluoropropyl group. However, in component (A-2), at least two of $R^1$ in a molecule are the alkenyl groups described above, and preferably vinyl groups. It should be noted that it is preferable that 0.1 to 40 mol % of all of $R^1$ in a molecule is the alkenyl group. When the proportion of the alkenyl groups is greater than or equal to the minimum value of the range given above, the reactivity with component (B) is improved. When the proportion of the alkenyl groups is less than or equal to the maximum value of the range given above, the reactivity with component (B) is improved. However, in component (A-2), at least one of $R^1$ in a molecule is the aryl group described above, and preferably a phenyl group. It is preferable that greater than or equal to 10 mol % of all of $R^1$ in a molecule is the alkyl group and it is particularly preferable that it is a methyl group, because light attenuation due to refraction, reflection, scattering and the like is small for the cured product obtained by curing the present composition.

X in the formula is a hydrogen atom or an alkyl group. When X is an alkyl group, it is preferably an alkyl group having from 1 to 3 carbons. Specific examples are methyl, ethyl and propyl groups.

In the formula, "a" is a number of 0 to 0.3, "b" is 0 or a positive number, "c" is a positive number, "d" is a positive number, and "e" is a number of 0 to 0.4, and they satisfy: a+b+c+d=1, c/d is a number of 0 to 10 and b/d is a number of 0 to 0.5.

The molecular weight of component (A-2) is not particularly limited, but it is preferable that mass average molecular weight (Mw) calibrated against polystyrene standards is preferably within a range of 500 to 100,000, and it is particularly preferable that it is within a range of 1,000 to 30,000.

Such component (A-2) is preferably an organopolysiloxane including $R^1(CH_3)_2SiO_{1/2}$ units and $SiO_{4/2}$ units. Component (A-2) may include $R^1SiO_{3/2}$ units or $R^1(CH_3)SiO_{2/2}$ units in a range without departing from the scope of the present invention.

In component (A-2), the ratio of $R^1(CH_3)_2SiO_{1/2}$ units and $SiO_{4/2}$ units is not particularly limited, but it is preferable that the ratio of $R^1(CH_3)_2SiO_{1/2}$ units to $SiO_{4/2}$ units is within a range of 0.5 to 3 and more preferable within a range of 0.8 to 2. When the ratio of $R^1(CH_3)_2SiO_{1/2}$ units to $SiO_{4/2}$ units is greater than or equal to the minimum value of the range given above, the mechanical strength of the cured product obtained is good. When the ratio is less than or equal to the maximum value of the range given above, the miscibility of component (A-2) toward component (A-1) is improved.

The content of component (A-2) is an amount such that the mass ratio of component (A-2) to component (A-1) is within a range of 1/99 to 99/1 and preferably within a range of 1/9 to 9/1. When the content of component (A-2) is greater than or equal to the minimum value of the range given above, mechanical strength of the cured product obtained is good, while when it is less than or equal to the maximum value of the range given above, handling and processability of the composition obtained is good.

Component (B) is an organopolysiloxane having at least two silicon-bonded hydrogen atoms in a molecule. The molecular structure of component (B) is not particularly limited and may be, for example, straight chain, straight chain having some branches, branched chain, resinoid, or cyclic.

Also, examples of the groups that bond to silicon atoms other than the hydrogen atoms in component (B) include: alkyl groups having from 1 to 12 carbons, such as a methyl group, an ethyl group, a propyl group, an isopropyl group, an n-butyl group, an isobutyl group, a tert-butyl group, an n-pentyl group, a neopentyl group, a hexyl group, a cyclohexyl group, a heptyl group, an octyl group, a nonyl group, a decyl group, an undecyl group, and a dodecyl group; aryl groups having from 6 to 20 carbons, such as a phenyl group, a tolyl group, a xylyl group, and a naphthyl group; aralkyl groups having from 7 to 20 carbons, such as a benzyl group, a phenethyl group, and a phenylpropyl group; and groups with halogen atoms, such as fluorine atoms, chlorine atoms and bromine atoms, substituting a portion of or all of the hydrogen atoms of these groups. It should be noted that the silicon atoms in component (B) may bond a small amount of hydroxyl groups and alkoxy groups such as methoxy groups and ethoxy groups without departing from the scope of the present invention.

A viscosity at 25° C. of component (B) is not limited, but is preferably in a range of 1 to 10,000 mPa·s and more preferably in a range of 5 to 1,000 mPa·s. When the viscosity of component (B) is greater than or equal to the minimum value of the range given above, mechanical strength of the cured product obtained is good, while when it is less than or equal to the maximum value of the range given above, handling and processability of the composition obtained is good.

Examples of component (B) include one type or two or more types selected from the group consisting of: 1,1,3,3-tetramethyldisiloxane, 1,3,5,7-tetramethylcyclotetrasiloxane, tris(dimethylhydrogensiloxy)methylsilane, tris(dimethylhydrogensiloxy)phenyl silane, 1-(3-glycidoxypropyl)-1,3,5,7-tetramethylcyclotetrasiloxane, 1,5-di(3-glycidoxypropyl)-1,3,5,7-tetramethylcyclotetrasiloxane, 1-(3-glycidoxypropyl)-5-trimethoxysilylethyl-1,3,5,7-tetramethylcyclotetrasiloxane, a methylhydrogenpolysiloxane terminated with trimethylsiloxy groups at both molecular terminals, a dimethylsiloxane-methylhydrogensiloxane copolymer terminated with trimethylsiloxy groups at both molecular terminals, a dimethylpolysiloxane terminated with dimethylhydrogensiloxy groups at both molecular terminals, a dimethylsiloxane-methylhydrogensiloxane copolymer terminated with dimethylhydrogensiloxy groups at both molecular terminals, a methylhydrogensiloxane-diphenylsiloxane copolymer terminated with trimethylsiloxy groups at both molecular terminals, a methylhydrogensiloxane-diphenylsiloxane-dimethyl siloxane copolymer terminated with trimethylsiloxy groups at both molecular terminals, a hydrolysis condensate of trimethoxysilane, a copolymer composed of $(CH_3)_2HSiO_{1/2}$ units and $SiO_{4/2}$ units, and a copolymer composed of $(CH_3)_2HSiO_{1/2}$ units and $SiO_{4/2}$ units and $(C_6H_5)SiO_{3/2}$ units.

Examples of component (B) include the following organosiloxanes. In the following formulas, Me and Ph denote a methyl group and a phenyl group, respectively. Each m and n is an integer greater than or equal to 1. Each "f", "g" and "h" is a positive number and the sum of "f", "g" and "h" or the sum of "f", "g", "h" and "i" is 1.

The content of component (B), per 1 mol of alkenyl groups in component (A), is in a range such that the silicon-bonded hydrogen atoms in component (B) is in a range of 0.1 to 10, and preferably in a range of 0.5 to 5. This is because an obtained composition is satisfactorily cured if the content of component (B) is not less than the minimum value of the above-mentioned range, and heat resistance of an obtained cured product is improved if the content of component (B) is not more than the maximum value of the above-mentioned range.

Component (C) is an organopolysiloxane having at least one aryl group in a molecule, and a metal atom selected from the group consisting of V, Ta, Nb and Ce, and is a component to suppress the formation of cracks in the cured product obtained from the present composition by thermal aging.

Examples of the groups that bond to silicon atoms in component (C) include: alkyl groups having from 1 to 12 carbons, such as a methyl group, an ethyl group, a propyl group, an isopropyl group, an n-butyl group, an isobutyl group, a tert-butyl group, an n-pentyl group, a neopentyl group, a hexyl group, a cyclohexyl group, a heptyl group, an octyl group, a nonyl group, a decyl group, an undecyl group, and a dodecyl group; alkenyl groups having from 2 to 12 carbons, such as a vinyl group, an allyl group, a butenyl group, a pentenyl group, a hexenyl group, a heptenyl group, an octenyl group, a nonenyl group, a decenyl group, undecenyl group and a dodecenyl group; aryl groups having from 6 to 20 carbons, such as a phenyl group, a tolyl group, a xylyl group, and a naphthyl group; aralkyl groups having from 7 to 20 carbons, such as a benzyl group, a phenethyl group, and a phenylpropyl group; and groups with halogen atoms, such as fluorine atoms, chlorine atoms and bromine atoms, substituting a portion of or all of the hydrogen atoms of these groups. In particular, component (C) preferably has at least one aryl group in a molecule and the content of the aryl group is at least 5 mol % or preferably at least 10 mol %, based on the total of silicon-bonded organic groups.

Such component (C) may be prepared by the reactions between chloride or carboxylic acid salt of Ce, or alkoxide or chloride of V, Ta or Nb, and alkali metal salt of organopolysiloxane containing silanol groups, for example.

Examples of the chloride or carboxylic acid salt of Ce described above include: cerium chloride, cerium 2-ethylhexanoate, cerium naphthenate, cerium oleate, cerium laurate and cerium stearate.

Also, examples of alkoxide or chloride of V, Ta or Nb include: tantalum chloride, tantalum ethoxide, tantalum butoxide, vanadium oxytrichloride, vanadium oxydichloride, vanadium trichloride, vanadium tribromide, niobium chloride, niobium ethoxide, and niobium butoxide.

Also, examples of the alkali metal salt of organopolysiloxane containing silanol groups described above include: potassium salt of diorganopolysiloxane terminated with silanol groups at both molecular terminals, sodium salt of diorganopolysiloxane terminated with silanol groups at both molecular terminals, potassium salt of diorganopolysiloxane terminated with a silanol group at one end and terminated with a triorganosiloxy group at the other end, and sodium salt of diorganopolysiloxane terminated with a silanol group at one end and terminated with a triorganosiloxy group at the other end.

Meanwhile, examples of the groups that bond to silicon atoms in the organopolysiloxane include: alkyl groups having from 1 to 12 carbons, such as a methyl group, an ethyl group, a propyl group, an isopropyl group, an n-butyl group, an isobutyl group, a tert-butyl group, an n-pentyl group, a neopentyl group, a hexyl group, a cyclohexyl group, a heptyl group, an octyl group, a nonyl group, a decyl group, an undecyl group, and a dodecyl group; aryl groups having from 6 to 20 carbons, such as a phenyl group, a tolyl group, a xylyl group, and a naphthyl group; aralkyl groups having from 7 to 20 carbons, such as a benzyl group, a phenethyl group, and a phenylpropyl group; and groups with halogen atoms, such as fluorine atoms, chlorine atoms and bromine atoms, substituting a portion of or all of the hydrogen atoms of these groups. It should be noted that the organopolysiloxane has at least one aryl group in a molecule.

The reaction described above can be carried out in an organic solvent, including alcohols such as methanol, ethanol, isopropanol, butanol, and methoxyisopropanol; aromatic hydrocarbons such as toluene and xylene; aliphatic hydrocarbons such as hexane and heptane; mineral spirits, ligroin, petroleum ether and the like, at room temperature or at an elevated temperature. Also, it is preferable that the organic solvent and the low-boiling components are optionally removed from the obtained reaction product, or the precipitates are optionally filtered out from the obtained reaction product. Additionally, dialkylformamide, hexaalkylphosphoric amide and the like may be added to promote the reaction. The content of the metal atoms in the organopolysiloxane prepared as above is preferably in a range of 0.1 to 5 mass %.

The content of component (C) in the present composition is such that the content of V, Ta, Nb or Ce atoms is in a range of 20 to 2,000 ppm, preferably in a range of 20 to 1,500 ppm, more preferably in a range of 20 to 1,250 ppm, and particularly preferably in a range of 20 to 1,000 ppm, in terms of mass units. If the content of component (C) is not less than the minimum value of the range given above, the heat resistance of the obtained composition can be improved and the coloration of the lead frame in an optical semiconductor device can be suppressed. Meanwhile, if the content of component (C) is not more than the maximum value of the range given above, the change in the luminescent color can be reduced when used in an optical semiconductor device.

Component (D) is a hydrosilylation catalyst used to accelerate hydrosilylation reaction of the present composition. Such component (D) is preferably a platinum element catalyst and a platinum element compound catalyst, and examples include platinum-based catalysts, rhodium-based catalysts, and palladium-based catalysts. Platinum-based catalyst are preferred because hydrosilylation reactions are significantly accelerated. Examples of such platinum-based catalysts include platinum fine powders, platinum black, chloroplatinic acid, alcohol-modified products of chloroplatinic acid, complexes of chloroplatinic acid and diolefin, platinum-olefin complexes, platinum-carbonyl complexes such as platinum bis-(acetoacetate) and platinum bis-(acetylacetonate), chloroplatinic acid-alkenylsiloxane complexes such as chloroplatinic acid-divinyltetramethyldisiloxane complexes and chloroplatinic acid-tetravinyltetramethylcyclotetrasiloxane complexes, platinum-alkenylsiloxane complexes such as platinum-divinyltetramethyldisiloxane complexes and platinum-tetravinyltetramethylcyclotetrasiloxane complexes, and complexes of chloroplatinic acid and acetylene alcohols. Platinum-alkenylsiloxane complexes are particularly preferable due to their excellent effect of accelerating hydrosilylation reactions. One type of these hydrosilylation reaction catalysts may be used alone, or two or more types may be used in combination.

The alkenylsiloxane used in the platinum-alkenylsiloxane complex is not particularly limited, and examples include 1,3-divinyl-1,1,3,3-tetramethyldisiloxane, 1,3,5,7-tetramethyl-1,3,5,7-tetravinylcyclotetrasiloxane, alkenylsiloxane oligomers in which some of the methyl groups of these alkenylsiloxanes are substituted with ethyl groups, phenyl groups, or the like, and alkenylsiloxane oligomers in which the vinyl groups of these alkenylsiloxanes are substituted with allyl groups, hexenyl groups, or the like. In particular, 1,3-divinyl-1,1,3,3-tetramethyldisiloxane is preferable due to the favorable stability of the platinum-alkenylsiloxane complex that is produced.

In order to improve the stability of the platinum-alkenylsiloxane complexes, it is preferable to dissolve these platinum-alkenylsiloxane complexes in an alkenylsiloxane oligomer such as 1,3-divinyl-1,1,3,3-tetramethyldisiloxane, 1,3-diallyl-1,1,3,3-tetramethyldisiloxane, 1,3-divinyl-1,3-dimethyl-1,3-diphenyldisiloxane, 1,3-divinyl-1,1,3,3-tetraphenyldisiloxane, or 1,3,5,7-tetramethyl-1,3,5,7-tetravinylcyclotetrasiloxane or an organosiloxane oligomer such as a dimethylsiloxane oligomer, and it is particularly preferable to dissolve the complexes in an alkenylsiloxane oligomer.

The content of component (D) is a catalytic quantity. Specifically, the content of component (D) is, in terms of mass units, an amount such that the amount of metal atoms in component (D) is preferably in a range of 0.01 to 500 ppm, more preferably in a range of 0.01 to 100 ppm, and particularly preferably in a range of 0.1 to 50 ppm. The coloration of the cured product can be suppressed when the content of component (D) is within the range described above. An obtained composition is satisfactorily cured if the content of component (D) is not less than the minimum value of the range given above, and the coloration of an obtained cured product is improved if the content of component (D) is not more than the maximum value of the range given above.

The present composition may include a hydrosilylation reaction suppressing agent as a component (E) as an optional component in order to prolong the usable time at ambient temperature and to improve storage stability. Examples of such component (E) include alkyne alcohols such as 1-ethynylcyclohexan-1-ol, 2-methyl-3-butyn-2-ol, 3,5-dimethyl-1-hexyn-3-ol, and 2-phenyl-3-butyn-2-ol; enyne compounds such as 3-methyl-3-penten-1-yne and 3,5-dimethyl-3-hexen-1-yne; methylalkenylsiloxane oligomers such as 1,3,5,7-tetramethyl-1,3,5,7-tetravinylcyclotetrasiloxane and 1,3,5,7-tetramethyl-1,3,5,7-tetrahexenylcyclotetrasiloxane; alkynoxysilanes such as dimethyl bis-(3-methyl-1-butyn-3-oxy)silane and methylvinyl bis-(3-methyl-1-butyn-3-oxy)silane, and triallylisocyanurate-based compounds.

The content of component (E) is not particularly limited but is an amount sufficient to suppress gelling or to suppress curing at the time of the mixing of components (A) to (C) and, furthermore, is an amount sufficient to enable long-term storage. Specifically, the content of component (E) is preferably within the range of from 0.0001 to 5 parts by mass and more preferably within the range of from 0.01 to 3 parts by mass per 100 parts by mass of the total of components (A) to (C). This is because the sufficient pot-life can be maintained if the content of component (E) is not less than the minimum value of the range given above, while the prompt curing can be achieved by heating if the content of component (E) is not more than the maximum value of the range given above.

In addition, the present composition may also contain an adhesion promoter (F) in order to further improve adhesion to the substrate with which the composition makes contact during curing. Such component (F) is preferably an organic silicon compound having 1 or 2 or more silicon-bonded alkoxy groups in a molecule. Examples of the alkoxy groups include methoxy groups, ethoxy groups, propoxy groups, butoxy groups, and methoxyethoxy groups, and methoxy groups or ethoxy groups are particularly preferable. Examples of groups other than alkoxy groups bonding with the silicon atoms of this organic silicon compound include substituted or unsubstituted monovalent hydrocarbon groups such as alkyl groups, alkenyl groups, aryl groups, aralkyl groups, and halogenated alkyl groups; glycidoxyalkyl groups such as 3-glycidoxypropyl groups and 4-glycidoxybutyl groups; epoxycyclohexylalkyl groups such as 2-(3,4-epoxycyclohexyl)ethyl groups and 3-(3,4-epoxycyclohexyl) propyl groups; epoxy group-containing monovalent organic groups such as oxyranylalkyl groups such as 4-oxyranylbutyl groups and 8-oxyranyloctyl groups; acrylic group-containing monovalent organic groups such as 3-methacryloxypropyl groups; isocyanate groups; isocyanurate groups; and hydrogen atoms. The organic silicon compound preferably has a group that can react with the aliphatic unsaturated hydrocarbon groups or silicon-bonded hydrogen atoms in the present composition. Specifically, the organic silicon compound preferably has silicon-bonded aliphatic unsaturated hydrocarbon groups or silicon-bonded hydrogen atoms.

The content of component (F) is not particularly limited, but the content is preferably within a range of 0.01 to 10 parts by mass and more preferably within a range of 0.1 to 3 parts by mass per 100 parts by mass of the total of components (A) to (C). When the content of component (F) is not less than the minimum value of the range given above, adhesion is good and when the content of component (F) is not more than the maximum value of the range given above, storage stability is good.

This composition may also contain a fluorescent substance (G) as an optional component. Examples of such component (G) include yellow, red, green, and blue light emitting fluorescent substances composed of oxide-based fluorescent substances, oxynitride-based fluorescent substances, nitride-based fluorescent substances, sulfide fluorescent substances, oxysulfide-based fluorescent substances, or the like, which are widely used in light emitting diodes (LEDs). Examples of oxide-based fluorescent substances include yttrium, aluminum, and garnet-based YAG green to yellow light-emitting fluorescent substances containing cerium ions; terbium, aluminum, and garnet-based TAG yellow light-emitting fluorescent substances containing cerium ions; and silicate green to yellow light-emitting fluorescent substances containing cerium or europium ions. Examples of oxynitride-based fluorescent substances include silicon, aluminum, oxygen, and nitrogen-based SiAlON red to green light-emitting fluorescent substances containing europium ions. Examples of nitride-based fluorescent substances include calcium, strontium, aluminum, silicon, and nitrogen-based CASN red light-emitting fluorescent substances containing europium ions. Examples of sulfide-based fluorescent substances include ZnS-based green light-emitting fluorescent substances containing copper ions or aluminum ions. Examples of oxysulfide-based fluorescent substances include $Y_2O_2S$-based red light-emitting fluorescent substances containing europium ions. These fluorescent substances may be used as one type or as a mixture of two or more types.

Furthermore, the average particle diameter of component (G) is not particularly limited but is preferably in a range of 1 to 50 µm and more preferably in a range of 5 to 20 m. This is because the viscosity increase during mixing is suppressed if the average particle diameter of component (G) is not less than the minimum value of the range given above, and the light transmittance is good if the average particle diameter of component (G) is not more than the maximum value of the range given above.

The content of component (G) is not particularly limited, but it is in a range of 0.1 to 70 mass % based on the total mass of the present composition. It is preferable that the content is not more than 70 mass % because of the handling workability, and it is preferable that the content is not less than 5 mass % considering the light conversion to white light.

The present composition may also contain 1 or more types of components selected from: 1 or more types of inorganic fillers selected from silica, glass, alumina, and the like; silicone rubber powders; resin powders such as silicone resins and polymethacrylate resins; and 1 or more types of components selected from heat resistant agents, dyes, pigments, flame retardants, solvents, and the like as other optional components, as long as the object of the present invention is not undermined.

The present composition is such that curing occurs either at room temperature or under heating, but it is preferable to heat the composition in order to achieve rapid curing. The heating temperature is preferably in a range of 50 to 200° C.

The present composition preferably forms a cured product with a type A durometer hardness from 30 to 99 and more preferably from 35 to 95 as prescribed by JIS K 6253 when cured. This is because the cured product of the curable silicone composition has a strength for enough protection if its hardness is not less than the minimum value of the range given above, and the cured product of the curable silicone composition has compliance for enough durability if its hardness is not more than the maximum value of the range given above.

Furthermore, the present composition is preferably cured to produce a cured product that has an optical transmittance not less than 90% at 450 nm. This optical transmittance can be found, for example, by measuring the optical transmittance (25° C.) of the cured product with a spectrophotometer at an optical path length of 0.1 cm and a wavelength of 450 nm.

The present composition preferably produces the cured product, which has a value of b* not more than 2.0, and particularly preferably produces the cured product, which has a value of b* not more than 1.0, in the CIE L*a*b* color space defined in JIS Z 8730, before and after being heated at 240° C. for 500 hours. It should be noted that, for the cured product of the present invention, the value of b* in the CIE L*a*b* color space defined in JIS Z8730 can be measured by a chromameter, for example.

[Cured Product]

A cured product of the present invention will now be described in detail.

The cured product of the present invention can be obtained by curing the curable silicone composition described above. The cured product of the present invention preferably has characteristics as described above. The cured product of the present invention may be a sheet-like or a film-like cured product, or a cured product coating on a transparent substrate such as a glass substrate. Examples of a method to form the cured product include compression molding, transfer molding, injection molding and deposition on a transparent substrate. The curable silicone composition described above can be mixed using a mixing device such as a static mixer or a screw mixer, and molded by injecting into a molding device.

It should be noted that the molding conditions are not particularly limited, but the curable silicone composition can be cured at the temperature in a range of 50 to 200° C., or preferably in a range of 70° C. to 180° C., and for 30 seconds to 30 minutes, or preferably for 1 minute to 10 minutes. Also, post-curing (secondary curing) can be performed at the temperature in a range of 50 to 200° C., or preferably in a range of 70 to 180° C., and for 0.1 to 10 hours, or preferably for about 1 to 4 hours.

Figure 5:
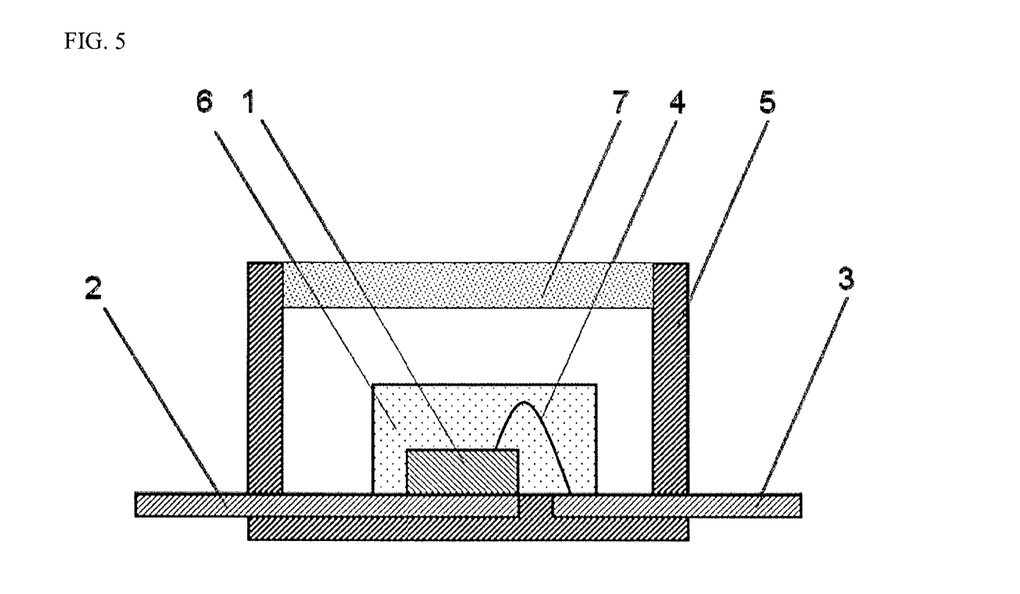
FIG. 5 is a cross-sectional view of an LED that uses a cured product of the present invention containing a fluorescent substance as a remote phosphor.

When the cured product of the present invention contains fluorescent substances, the cured product can be used as a remote phosphor or a phosphor sheet for a LED or an illumination apparatus. A remote phosphor is a cured product containing a fluorescent substance, which is used for obtaining white or 'light bulb color' from a blue color light emitted from an LED chip at a position far from the LED chip or the LED device, and used for diffusing the highly-directional light emitted from the LED chip. FIG. 5 is a cross-sectional view of an LED that uses a cured product of the present invention containing a fluorescent substance as a remote phosphor. In the LED illustrated in FIG. 5, an optical semiconductor element 1 is die-bonded to a lead frame 2, and this optical semiconductor element 1 and a lead frame 3 are wire-bonded together by a bonding wire 4. This optical semiconductor element 1 may be sealed by a cured product 6 of the curable silicone composition described above. A light reflection material 5 is formed around the optical semiconductor element 1. A cured product 7 of the curable silicone composition containing a fluorescent substance described above is disposed as a remote phosphor above the semiconductor element 1 with a space between them in the light reflection material 5.

Figure 6:
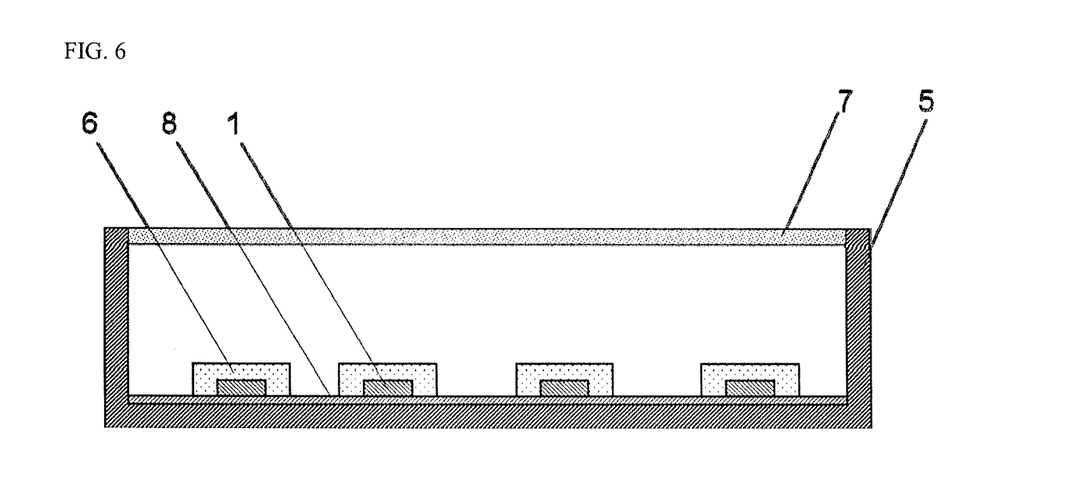
FIG. 6 is a cross-sectional view of an illumination apparatus that uses a cured product of the present invention containing a fluorescent substance as a remote phosphor.

FIG. 6 is a cross-sectional view of an illumination apparatus that uses a cured product of the present invention containing a fluorescent substance as a remote phosphor. In the illumination apparatus illustrated in FIG. 6, optical semiconductor elements 1 are die-bonded on a substrate 8 and connected electrically to a circuit (not illustrated) on the substrate. These optical semiconductor elements 1 may be sealed by a cured product 6 of the curable silicone composition described above. A light reflection material 5 is formed around the substrate 8 having a plurality of the optical semiconductor elements 1. A cured product 7 of the curable silicone composition containing a fluorescent substance described above is disposed as a remote phosphor above the semiconductor elements 1 with a space between them in a light reflection material 5. Examples of the substrate 8 include, highly electrically conductive metals such as silver, gold, and copper; low-electrically conductive metals such as aluminum, and nickel; thermoplastic resins such as PPA, and LCP intermixed with white pigments; thermoplastic resins such as epoxy resins, BT resins, polyimide resins, and silicone resins including white pigment; ceramics such as alumina, aluminum nitride; and the like.

Also, the cured product of the present invention can be used as a lens material when the cured product does not contain a fluorescent substance.

[Optical Semiconductor Device]

An optical semiconductor device of the present invention will now be described in detail.

The optical semiconductor device of the present invention is characterized by the optical semiconductor element being sealed, coated or bonded by the composition described above. Specific examples of the optical semiconductor element include, a light emitting diode (LED), a semiconductor laser, a photo-diode, a photo-transistor, a solid-state imaging sensor, and an emitter and a receptor for a photocoupler. A light emitting diode (LED) is particularly preferable. Examples of the light emitting diode (LED) include, an SMD (Surface Mount Device) type and a COB (Chip On Board) type. Examples of the SMD type include, top-view type and side-view type. Examples of the optical semiconductor elements include light emitting diode (LED) chips and solid-state image sensing elements.

Examples of the light emitting diode (LED) chip include, face-up type and flip-chip type, and further include, an infrared LED chip containing gallium-arsenide, a red LED chip containing gallium-aluminum-arsenide, an orange LED chip or a yellow LED chip containing gallium-arsenide-phosphorus, a yellow-green LED chip containing gallium-phosphorus doped with nitrogen, and a blue or blue-violet LED chip containing gallium-nitride-based compound.

Since light emission occurs from the top, bottom, left, and right sides of the semiconductor in a light-emitting diode (LED), it is not preferable for the parts constituting the light-emitting diode (LED) to absorb light, and a material with high optical transmittance or high reflectivity is preferable. Therefore, it is also preferable for the substrate on which the optical semiconductor element is mounted to be a material with high optical transmittance or high reflectivity. Examples of the substrate on which this optical semiconductor element is mounted include, highly electrically conductive metals such as silver, gold, and copper; low-electrically conductive metals such as aluminum, and nickel; thermoplastic resins such as PPA, and LCP intermixed with white pigments; thermoplastic resins such as epoxy resins, BT resins, polyimide resins, and silicone resins including white pigment; ceramics such as alumina, aluminum nitride; and the like. The curable silicone composition has favorable thermal shock resistance with respect to the optical semiconductor element and the substrate, and the resulting optical semiconductor device can demonstrate good reliability.

FIG. 1 to 4 illustrate cross-sectional views of a surface mounted type LED, which is one example of the optical semiconductor device of the present invention. In the LED illustrated in FIG. 1, an optical semiconductor element 1 is die-bonded to a lead frame 2, and this optical semiconductor element 1 and a lead frame 3 are wire-bonded together by a bonding wire 4. A light reflection material 5 is formed around the optical semiconductor element 1. The optical semiconductor element 1 inside the light reflection material 5 is sealed by a cured product 6 of the curable silicone composition described above.

Figure 2:
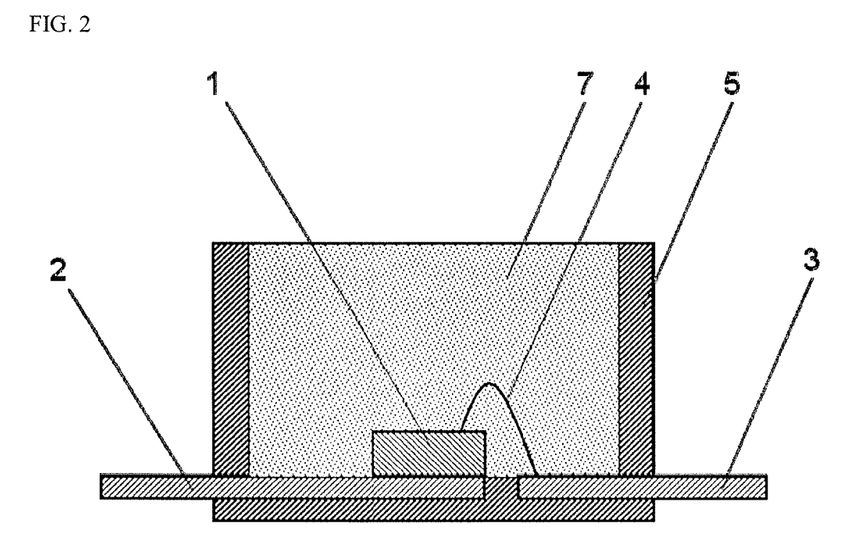
FIG. 2 is a cross-sectional view of an LED that is an example of an optical semiconductor device of the present invention.
Figure 3:
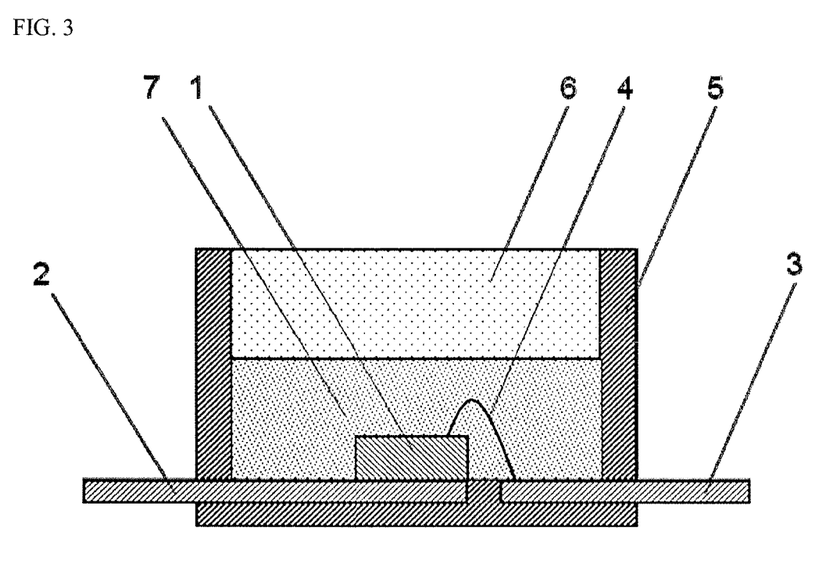
FIG. 3 is a cross-sectional view of an LED that is an example of an optical semiconductor device of the present invention.
Figure 4:
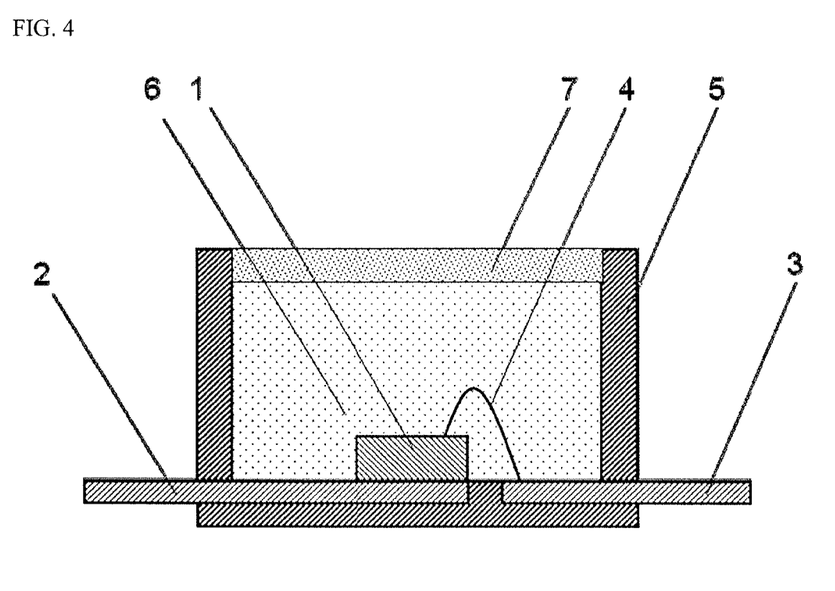
FIG. 4 is a cross-sectional view of an LED that is an example of an optical semiconductor device of the present invention.

For the LED illustrated in FIG. 2, an optical semiconductor element 1 is sealed by a cured product 7 of the curable silicone composition described above containing a fluorescent substance. For the LED illustrated in FIG. 3, an optical semiconductor element 1 is sealed by a cured product 7 of the curable silicone composition described above containing a fluorescent substance, and the surface of the cured product 7 is further sealed by a cured product 6 of the curable silicone composition described above. For the LED illustrated in FIG. 4, an optical semiconductor element 1 is sealed by a cured product 6 of the curable silicone composition described above, and the surface of the cured product 6 is further sealed by a cured product 7 of the curable silicone composition described above containing a fluorescent substance.

Figure 1:
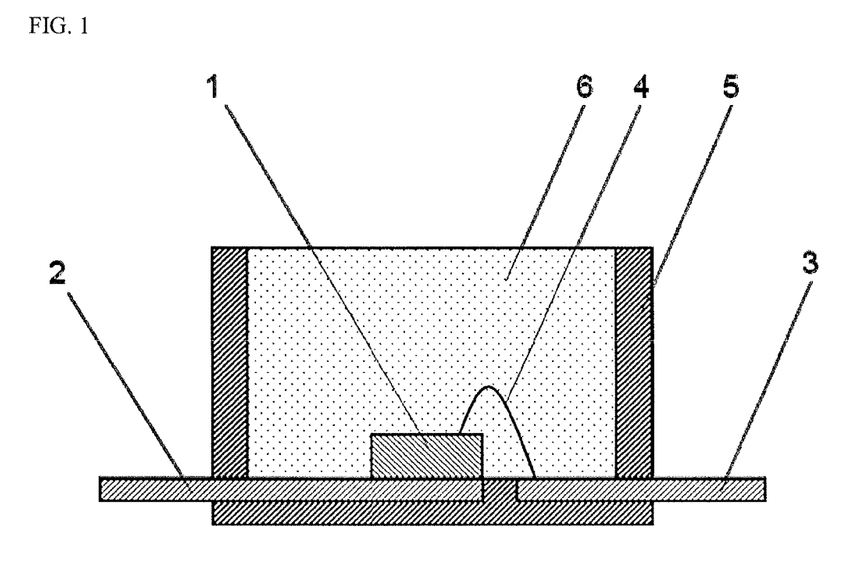
FIG. 1 is a cross-sectional view of an LED that is an example of an optical semiconductor device of the present invention.

Examples of methods to produce a surface mounted type LED illustrated in FIG. 1 include a method in which the optical semiconductor element 1 is die-bonded to the lead frame 2, the optical semiconductor element 1 and the lead frame 3 are wire-bonded using a gold bonding wire 4, then the curable silicone composition is molded by transfer molding or compression molding to form the light reflection material 5 around the optical semiconductor element 1. Examples of the methods further include a method, in which the optical semiconductor element 1 inside the light reflection material 5 is resin-sealed with the curable silicone composition described above after the light reflection material 5 is formed.

EXAMPLES

The curable silicone composition, the cured product thereof, and the optical semiconductor device of the present invention will be described in detail hereinafter using examples. It should be noted that, in the examples, the viscosity is the value at 25° C., and Me, Vi, Ph, and Ep respectively represent a methyl group, a vinyl group, a phenyl group, and a 3-glycidoxypropyl group. The characteristics of the cured product of the curable silicone composition were measured as follows.

[Thermal Stability of Cured Product]

A sheet-like cured product of 2 mm in thickness was prepared and left in an oven at 150° C. for 1,000 hours. The transparency at 450 nm was measured by a haze meter and compared with an initial value for its decrease.

[Weight Loss of Cured Product]

A sheet-like cured product of 2 mm in thickness was prepared and left in an oven at 170° C. for 1,000 hours. The weight loss was compared with an initial value for its decrease.

[Hardness Change of Cured Product]

A sheet-like cured product of 2 mm in thickness was prepared and left in an oven at 170° C. for 1,000 hours. The storage elastic modulus at 25° C. was measured by a dynamic analyzer, and compared with an initial value for the ratio of its change. When the ratio of the change was in a range from 100 to 300%, it was rated as ⊚, and when it was 300% or greater, it was rated as ×.

Reference Example 1

82.2 g (0.44 mol) of 1,3-divinyl-1,1,3,3-tetramethyldisiloxane, 143 g of water, 0.38 g of trifluoromethane sulfonic acid, and 500 g of toluene were loaded into a 4-necked flask with an agitator, a refluxing condenser, and a thermometer, and 524.7 g (2.65 mol) of phenyltrimethoxysilane was added dropwise into the mixture over the course of one hour while stirring. After dropwise addition was complete, the mixture was heat-refluxed for one hour. The mixture was then cooled, and after the bottom layer was separated, the toluene solution layer was washed with water three times. Next, 314 g (1.42 mol) of 3-glycidoxypropyl methyldimethoxysilane, 130 g of water, and 0.50 g of potassium hydroxide were added to the water-washed toluene solution layer, and the mixture was heat-refluxed for one hour. Methanol was then distilled off, and the excess water was removed by azeotropic dehydration. After heat-refluxing for 4 hours, the toluene solution was cooled, neutralized with 0.55 g of acetic acid, and washed 3 times with water. After the water was removed, the toluene was distilled off under reduced pressure to prepare an adhesion promoter with a viscosity of 8,500 mPa·s represented by the average unit formula:

(Me$_2$ViSiO$_{1/2}$)$_{0.18}$(PhSiO$_{3/2}$)$_{0.53}$(EpMeSiO$_{2/2}$)$_{0.29}$.

Reference Example 2

To a phenylmethyloligosiloxane terminated with silanol groups at both molecular terminals, represented by the average formula:

HO(PhMeSiO)$_{5.4}$H, the equivalent amount of sodium methoxide/methanol solution (28 mass %) to the silanol group and the equivalent amount of toluene as the phenylmethyloligosiloxane terminated with silanol groups at both molecular terminals were added and heated up to 110° C. under the normal pressure to distill off the methanol and the corresponding sodium silanolate in toluene solution was obtained. Next, 0.5 equivalent amount of the trimethylchlorosilane to the silanol groups were added dropwise at room temperature and sodium silanolate represented by the average formula:

Me$_3$SiO(PhMeSiO)$_{5.4}$Na in toluene solution was obtained.

Then, the sodium silanolate in toluene solution was added dropwise to a mixture of cerium trichloride, toluene and methoxyisopropanol while stirring. The salt was filtered out after stirring at room temperature for 1 hour. The filtrate was distilled off at an elevated temperature under a reduced pressure, and the phenyl silicone containing cerium, the cerium content of which was 9.5 mass % measured by X-ray Fluorescence Analysis, was obtained.

Reference Example 3

To a phenylmethyloligosiloxane terminated with silanol groups at both molecular terminals, represented by the average formula:

HO(PhMeSiO)$_{5.4}$H, 0.5 equivalent mole amount of 1,3-divinyltetramethyldisilazane to the silanol groups and the catalytic amount of trifluoroacetate were added, stirred at an elevated temperature and the salt byproduct was filtered out at room temperature. Thereby, a phenylmethyloligosiloxane terminated with vinyl groups, in which half of the silanol groups were terminated with vinyldimethylsiloxy groups, represented by the average formula:

ViMe$_2$SiO(PhMeSiO)$_{5.4}$H was synthesized. The equivalent amount of sodium methoxide/methanol solution (28 mass %) to the silanol group and the equivalent weight of toluene as the phenylmethyloligosiloxane described above were added and heated up to 110° C. under the normal pressure to distill off the methanol and the corresponding sodium silanolate in toluene solution was obtained.

Then, the sodium silanolate in toluene solution described above was added dropwise to a mixture of cerium trichloride and tetrahydrofuran while stirring, stirred at room temperature for 1 hour, and further heated and stirred at 70° C. for 3 hours. The salt was filtered out at room temperature, the filtrate was distilled off at an elevated temperature under a reduced pressure, and the vinylphenylsilicone containing cerium, the cerium content of which was 9.4 mass % measured by X-ray Fluorescence Analysis, was prepared.

Reference Example 4

67 parts by mass of dimethylpolysiloxane terminated with trimethylsiloxy groups at both molecular terminals with a viscosity of 20 mPa·s at 25° C., 33 parts by mass of potassium silanolate, synthesized from potassium hydroxide, and hexamethylcyclotrisiloxane and octamethylcyclotetrasiloxane, and 0.3 parts by mass of hexamethylphosphoramide were reacted at 115° C. under nitrogen gas flow for 1 hour. Then, 120 parts by mass of anhydrous xylene and 16 parts by mass of cerium 2-ethylhexanoate salt were added and reacted for 2.5 hours at the reflux temperature. Thereafter, the mixture was cooled down to room temperature, neutralized by adding 3 parts by mass of trimethylchlorosilane, and the solvent was distilled off at a reduced pressure. Thus, dimethylsilicone containing cerium, the cerium content of which was 1.4 mass % measured by X-ray Fluorescence Analysis, was prepared.

[Curable Silicone Composition]

The following components were used as component (A).

Component (A-1): An alkenylorganopolysiloxane (vinyl group content=4.66 mass %) represented by the average unit formula:

$$(Me_2ViSiO_{1/2})_{0.25}(PhSiO_{3/2})_{0.75}$$

Component (A-2): An alkenylorganopolysiloxane (vinyl group content=4.6 mass %) represented by the average unit formula:

$$(MePhViSiO_{1/2})_{0.23}(PhSiO_{3/2})_{0.77}$$

Component (A-3): A methylphenylpolysiloxane terminated with dimethylvinylsiloxy groups at both molecular terminals, which has a viscosity of 3,000 mPa·s (vinyl group content=1.8 mass %)

Component (A-4): An organopolysiloxane represented by the formula:

$$Ph_2ViSiO(Me_2SiO)_{12}SiPh_2Vi.$$

The following components were used as component (B).

Component (B-1): An organotrisiloxane (the content of hydrogen atoms bonded to silicon atoms=0.6 mass %) with a viscosity of 4 mPa·s represented by the formula:

$$HMe_2SiOPh_2SiOSiMe_2H$$

The following components were used as component (C).

Component (C-1): The phenylsilicone containing cerium prepared in Reference Example 2.

Component (C-2): The vinylphenylsilicone containing cerium prepared in Reference Example 3.

Component (C-3): A siloxane containing cerium represented by the formula:

$$Ce[OSiMe(OSiPh_2Me)_2]_3$$

(cerium content=6.7 mass %)

Component (C-4): The dimethylpolysiloxane containing cerium prepared in Reference Example 4 (cerium content=1.4 mass %).

Component (C-5): A siloxane containing tantalum represented by the formula:

$$Ta(OSiPh_2Me)_5$$

Component (C-6): A siloxane containing niobium represented by the formula:

$$Nb(OSiPh_2Me)_5$$

Component (C-7): A siloxane containing vanadium represented by the formula:

$$O=V(OSiPh_2Me)_2$$

The following components were used as component (D).

Component (D-1): solution of a platinum-1,3-divinyl-1,1,3,3-tetramethyldisiloxane complex in 1,3,5,7-tetramethyl-1,3,5,7-tetravinylcyclotetrasiloxane (the solution contains 0.1 mass % of platinum)

The following component was used as component (E).

Component (E-1): 1-ethynylcyclohexanol

The following component was used as component (F).

Component (F-1): The adhesion promoter prepared in Reference Example 1, represented by the formula:

$$(Me_2Vi\ SiO_{1/2})_{0.18}(PhSiO_{3/2})_{0.53}(EpMeSiO_{2/2})_{0.29}$$

(vinyl group content=3.5 mass %)

The following component was used as component (G).

Component (G-1): An aluminate-based green fluorescent substance with an average particle diameter of 13 μm Component (G-2): A nitride-based red fluorescent substance with an average particle diameter of 15 μm Example 1

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-1) (in an amount such that the content of cerium was 600 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Example 2

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Example 3

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-2) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Example 4

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-3) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Example 5

56.7 parts by mass of component (A-1), 15.0 parts by mass of component (A-3), 22.3 parts by mass of component (B-1) [such that the content of hydrogen atoms bonded to silicon atoms in component (B-1) was 0.9 moles relative to the total 1 mole of vinyl groups in components (A-1) and (A-3)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Comparative Example 1

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Comparative Example 2

56.7 parts by mass of component (A-1), 15.0 parts by mass of component (A-3), 22.3 parts by mass of component (B-1) [such that the content of hydrogen atoms bonded to silicon atoms in component (B-1) was 0.9 moles relative to the total 1 mole of vinyl groups in components (A-1) and (A-3)], 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

Comparative Example 3

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-4) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 1.

TABLE 1

| Item | Example | | | | | Comparative Example | | |
|---|---|---|---|---|---|---|---|---|
| | 1 | 2 | 3 | 4 | 5 | 1 | 2 | 3 |
| Initial transmittance at 450 nm (%) | 91 | 92 | 92 | 92 | 92 | 92 | 92 | 20 |
| Decrease in the transmittance after exposure at 150° C. for 1,000 hours (%) | 3 | 3 | 3 | 3 | 3 | 7 | 6 | 3 |
| Weight loss after exposure at 170° C. for 1,000 hours (%) | 1.0 | 1.0 | 1.0 | 0.9 | 0.9 | 2.2 | 2.1 | 1.0 |
| Hardness change after exposure at 150° C. for 1,000 hours | ◯ | ◯ | ◯ | ◯ | ◯ | X | X | X |

Example 6

57.0 parts by mass of component (A-2), 15.0 parts by mass of component (A-3), 23.0 parts by mass of component (B-1) [such that the content of hydrogen atoms bonded to silicon atoms in component (B-1) was 1.0 moles relative to the total 1 mole of vinyl groups in components (A-2) and (A-3)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 2.

Example 7

57.0 parts by mass of component (A-2), 15.0 parts by mass of component (A-3), 21.2 parts by mass of component (B-1) [such that the content of hydrogen atoms bonded to silicon atoms in component (B-1) was 0.9 moles relative to the total 1 mole of vinyl groups in components (A-2) and (A-3)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 2.

Comparative Example 4

57.0 parts by mass of component (A-2), 15.0 parts by mass of component (A-3), 23.0 parts by mass of component (B-1) [such that the content of hydrogen atoms bonded to silicon atoms in component (B-1) was 1.0 moles relative to the total 1 mole of vinyl groups in components (A-2) and (A-3)], 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 2.

Comparative Example 5

57.0 parts by mass of component (A-2), 15.0 parts by mass of component (A-3), 21.2 parts by mass of component (B-1) [such that the content of hydrogen atoms bonded to silicon atoms in component (B-1) was 0.9 moles relative to the total 1 mole of vinyl groups in components (A-2) and (A-3)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. The transmittance, the thermal stability, the weight loss and the hardness change of the cured product of the curable silicone composition were measured. The results were listed in Table 2.

TABLE 2

| | Category | | | |
| --- | --- | --- | --- | --- |
| | Example | | Comparative Example | |
| Item | 6 | 7 | 4 | 5 |
| Initial transmittance at 450 nm (%) | 92 | 91 | 92 | 92 |
| Decrease in the transmittance after exposure at 150° C. for 1,000 hours (%) | 3 | 2 | 11 | 11 |
| Weight loss after exposure at 170° C. for 1,000 hours (%) | 0.7 | 0.6 | 1.8 | 1.9 |
| Hardness change after exposure at 150° C. for 1,000 hours | ◯ | ◯ | X | X |

Example 8

56.7 parts by mass of component (A-1), 14.0 parts by mass of component (A-3), 1.0 parts by mass of component (A-4), 23.3 parts by mass of component (B-1) [such that the content of hydrogen atoms bonded to silicon atoms in component (B-1) was 1.0 moles relative to the total 1 mole of vinyl groups in components (A-1), (A-3) and (A-4)], component (C-1) (in an amount such that the content of cerium was 600 ppm in the present composition), 2.5 parts by mass of component (D-1), 0.02 parts by mass of component (E-1), and 2.5 parts by mass of component (F-1) were mixed to prepare a curable silicone composition. To 5 parts by mass of the curable silicone composition, 2.5 parts by mass of component (G-1) and 0.20 parts by mass of component (G-2) were mixed to prepare a curable silicone composition containing the fluorescent substances.

An optical semiconductor device of FIG. 1 was produced using the curable silicone composition. It should be noted that the curable silicone composition was cured by heating at 150° C. for 2 hours. While the optical semiconductor device obtained was switched on by applying 400 mA current, it was aged at the condition of 85° C. and 85% humidity. The light-extraction efficiency was compared after 1,000 hours of the operation. Also, absence or presence of coloring of the silver lead frame in the optical semiconductor device after 1,000 hours of the operation was evaluated using an optical microscope with the following criteria: When no coloration of the lead frame was observed, it was rated as ⊚. When partial coloration of the lead frame was observed, it was rated as ◯. When the total coloration of the lead frame was observed, it was rated as ×. These results are shown in Table 3.

Example 9

56.7 parts by mass of component (A-1), 14.0 parts by mass of component (A-3), 1.0 parts by mass of component (A-4), 23.3 parts by mass of component (B-1) [such that the content of hydrogen atoms bonded to silicon atoms in component (B-1) was 1.0 moles relative to the total 1 mole of vinyl groups in components (A-1), (A-3) and (A-4)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. To 5 parts by mass of the curable silicone composition, 2.5 parts by mass of component (G-1) and 0.20 parts by mass of component (G-2) were mixed to prepare a curable silicone composition containing the fluorescent substances.

Using this curable silicone composition, an optical semiconductor device was produced in the similar manner as the Example 8, and light extraction efficiency thereof and absence or presence of coloring of the silver lead frame thereof were listed in Table 3.

Example 10

56.7 parts by mass of component (A-1), 14.0 parts by mass of component (A-3), 1.0 parts by mass of component (A-4), 23.3 parts by mass of component (B-1) [such that the content of hydrogen atoms bonded to silicon atoms in component (B-1) was 1.0 moles relative to the total 1 mole of vinyl groups in components (A-1), (A-3) and (A-4)], component (C-3) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. To 5 parts by mass of the curable silicone composition, 2.5 parts by mass of component (G-1) and 0.20 parts by mass of component (G-2) were mixed to prepare a curable silicone composition containing the fluorescent substances.

Using this curable silicone composition, an optical semiconductor device was produced in the similar manner as the Example 8, and light extraction efficiency thereof and absence or presence of coloring of the silver lead frame thereof were listed in Table 3.

Example 11

56.7 parts by mass of component (A-1), 14.0 parts by mass of component (A-3), 1.0 parts by mass of component (A-4), 22.3 parts by mass of component (B-1) [such that the content of hydrogen atoms bonded to silicon atoms in component (B-1) was 0.9 moles relative to the total 1 mole of vinyl groups in components (A-1), (A-3) and (A-4)], component (C-1) (in an amount such that the content of cerium was 200 ppm in the present composition), 2.5 parts by mass of component (D-1), 0.02 parts by mass of component (E-1), and 2.5 parts by mass of component (F-1) were mixed to prepare a curable silicone composition. To 5 parts by mass of the curable silicone composition, 2.5 parts by mass of component (G-1) and 0.20 parts by mass of component (G-2) were mixed to prepare a curable silicone composition containing the fluorescent substances.

Using this curable silicone composition, an optical semiconductor device was produced in the similar manner as the Example 8, and light extraction efficiency thereof and absence or presence of coloring of the silver lead frame thereof were listed in Table 3.

Comparative Example 5

56.7 parts by mass of component (A-1), 14.0 parts by mass of component (A-3), 1.0 parts by mass of component (A-4), 23.3 parts by mass of component (B-1) [such that the content of hydrogen atoms bonded to silicon atoms in component (B-1) was 1.0 moles relative to the total 1 mole of vinyl groups in components (A-1), (A-3) and (A-4)], 2.5 parts by mass of component (D-1), 0.02 parts by mass of component (E-1), and 2.5 parts by mass of component (F-1) were mixed to prepare a curable silicone composition. To 5 parts by mass of the curable silicone composition, 2.5 parts by mass of component (G-1) and 0.20 parts by mass of component (G-2) were mixed to prepare a curable silicone composition containing the fluorescent substances.

Using this curable silicone composition, an optical semiconductor device was produced in the similar manner as the Example 8, and light extraction efficiency thereof and absence or presence of coloring of the silver lead frame thereof were listed in Table 3.

Comparative Example 6

56.7 parts by mass of component (A-1), 14.0 parts by mass of component (A-3), 1.0 parts by mass of component (A-4), 22.3 parts by mass of component (B-1) [such that the content of hydrogen atoms bonded to silicon atoms in component (B-1) was 0.9 moles relative to the total 1 mole of vinyl groups in components (A-1), (A-3) and (A-4)], 2.5 parts by mass of component (D-1), 0.02 parts by mass of component (E-1), and 2.5 parts by mass of component (F-1) were mixed to prepare a curable silicone composition. To 5 parts by mass of the curable silicone composition, 2.5 parts by mass of component (G-1) and 0.20 parts by mass of component (G-2) were mixed to prepare a curable silicone composition containing the fluorescent substances.

Using this curable silicone composition, an optical semiconductor device was produced in the similar manner as the Example 8, and light extraction efficiency thereof and absence or presence of coloring of the silver lead frame thereof were listed in Table 3.

TABLE 3

| | Category | | | | | |
|---|---|---|---|---|---|---|
| | Example | | | | Comparative Example | |
| Item | 8 | 9 | 10 | 11 | 5 | 6 |
| Light extraction efficiency (%) | 100 | 100 | 100 | 100 | 88 | 88 |
| Coloring of the lead frame | ◎ | ◎ | ◎ | ◎ | X | X |

Example 12

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-5) (in an amount such that the content of tantalum was 200 ppm in the present composition), and 2.5 parts by mass of component (D-1) were mixed to prepare a curable silicone composition. A cured product was prepared by curing the curable silicone composition in an oven at 150° C. The cured product was heated at 225° C. for 2 hours, then at 250° C. for 2 hours using a thermogravimetric analyzer (TGA), and the rate of mass loss per minute was measured. The results were listed in Table 4.

Example 13

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-6) (in an amount such that the content of niobium was 200 ppm in the present composition), and 2.5 parts by mass of component (D-1) were mixed to prepare a curable silicone composition. A cured product was prepared by curing the curable silicone composition in an oven at 150° C. The rate of mass loss for this cured product was measured and the results were listed in Table 4.

Example 14

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-7) (in an amount such that the content of vanadium was 200 ppm in the present composition), and 2.5 parts by mass of component (D-1) were mixed to prepare a curable silicone composition. A cured product was prepared by curing the curable silicone composition in an oven at 150° C. The rate of mass loss for this cured product was measured and the results were listed in Table 4.

Example 15

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], component (C-3) (in an amount such that the content of cerium was 200 ppm in the present composition), and 2.5 parts by mass of component (D-1) were mixed to prepare a curable silicone composition. A cured product was prepared by curing the curable silicone composition in an oven at 150° C. The rate of mass loss for this cured product was measured and the results were listed in Table 4.

Comparative Example 7

56.7 parts by mass of component (A-1), 15.0 parts by mass of component (A-3), 23.3 parts by mass of component (B-1) [such that the content of hydrogen atoms bonded to silicon atoms in component (B-1) was 1.0 moles relative to the total 1 mole of vinyl groups in components (A-1) and (A-3)], and 2.5 parts by mass of component (D-1) were mixed to prepare a curable silicone composition. A cured product was prepared by curing the curable silicone composition in an oven at 150° C. The rate of mass loss for this cured product was measured and the results were listed in Table 4.

TABLE 4

| | Category | | | | |
|---|---|---|---|---|---|
| | Example | | | | Comparative Example |
| Item | 12 | 13 | 14 | 15 | 7 |
| Rate of mass loss at 225° C. (×10⁻³%/min) | 4.0 | 4.7 | 3.4 | 2.3 | 4.9 |
| Rate of mass loss at 250° C. (×10⁻³%/min) | 8.1 | 8.6 | 7.0 | 2.5 | 14.8 |

INDUSTRIAL APPLICABILITY

The curable silicone composition of the present invention can form a cured product, which does not form a crack by thermal aging as well as exhibits little yellowing. Therefore, the curable silicone composition is suitable for a sealant, a coating or an adhesive for an optical semiconductor element in an optical semiconductor device.

REFERENCE SIGNS LIST

1 Optical semiconductor element
2 Lead frame
3 Lead frame
4 Bonding wire
5 Light reflection material
6 Cured product of the curable silicone composition containing no fluorescent substance
7 Cured product of the curable silicone composition containing a fluorescent substance
8 Substrate

The invention claimed is:
1. A curable silicone composition comprising:
   (A) an organopolysiloxane having at least two alkenyl groups and at least one aryl group in a molecule;
   (B) an organopolysiloxane having at least two silicon-bonded hydrogen atoms in a molecule, in an amount such that the silicon-bonded hydrogen atoms in component (B) is from 0.1 to 10 moles per 1 mole of the alkenyl groups in component (A);
   (C) an organopolysiloxane having at least one aryl group in a molecule and a metal atom selected from the group consisting of V, Ta, Nb, and Ce, in an amount such that the metal atom in component (C) is from 20 to 2,000 ppm in terms of mass units based on the content of the composition; and
   (D) a catalytic amount of hydrosilylation reaction catalyst.
2. The curable silicone composition according to claim 1, wherein component (A) is a mixture comprising (A-1) a straight-chain organopolysiloxane having at least two alkenyl groups and at least one aryl group in a molecule; and (A-2) an organopolysiloxane represented by the following average unit formula:

wherein R¹ is each independently an alkyl group having from 1 to 12 carbons, an alkenyl group having from 2 to 12 carbons, an aryl group having from 6 to 20 carbons, an aralkyl group having from 7 to 20 carbons, or a group with halogen atoms substituting a portion of or all of hydrogen atoms thereof; at least two R¹ in a molecule are the alkenyl groups; X is a hydrogen atom or an alkyl group; and "a" is a number of 0 to 0.3, "b" is 0 or a positive number, "c" is a positive number, "d" is a positive number, and "e" is a number of 0 to 0.4, a+b+c+d=1, c/d is a number of 0 to 10, and b/d is a number of 0 to 0.5; in an amount such that a mass ratio of component (A-1) to component (A-2) is from 1/99 to 99/1.
3. The curable silicone composition according to claim 2, wherein component (A-2) includes: an alkenyl group having from 2 to 12 carbons in an amount from 0.1 to 40 mol % of the total amount of R¹; and an alkyl group having from 2 to 12 carbons in an amount not less than 10 mol % of the total amount of R¹.
4. The curable silicone composition according to claim 2, wherein component (A-2) is an organopolysiloxane including: R¹(CH₃)₂SiO₁/₂ units and SiO₄/₂ units, wherein R¹ is an alkyl group having from 1 to 12 carbons, an alkenyl group having from 2 to 12 carbons, an aryl group having from 6 to 20 carbons, an aralkyl group having from 7 to 20 carbons, or a group with halogen atoms substituting a portion of or all of hydrogen atoms thereof, and at least two of R¹ in a molecule are the alkenyl groups.
5. The curable silicone composition according to claim 1, further comprising (E) a hydrosilylation reaction inhibitor, in an amount from 0.01 to 3 parts by mass per 100 parts by mass of the total of components (A) to (C).
6. The curable silicone composition according to claim 1, further comprising (F) an adhesion promoter, in an amount from 0.1 to 3 parts by mass per 100 parts by mass of the total of components (A) to (C).
7. The curable silicone composition according to claim 1, further comprising (G) a fluorescent substance, in an amount from 0.1 to 70 mass % of the composition.
8. The curable silicone composition according to claim 1, wherein light transmittance of the composition is not less than 90% at 450 nm.

9. The curable silicone composition according to claim 1, wherein the composition forms a cured product having a value of b* in the CIE L* a* b* color space defined in JIS Z 8730 of not more than 2.0, before and after being heated at 240° C. for 500 hours.

10. A cured product, formed by curing the curable silicone composition according to claim 1.

11. An optical semiconductor device comprising an optical semiconductor element sealed, covered or adhered by the curable silicone composition according to claim 1.

12. The optical semiconductor device according to claim 11, wherein the optical semiconductor element is a light emitting diode.

13. The curable silicone composition according to claim 1, wherein the content of component (A-2) is an amount such that a mass ratio of component (A-2) to component (A-1) is from 1/9 to 9/1.

14. The curable silicone composition according to claim 1, wherein the alkenyl group in component (A) is a vinyl group and the aryl group in component (A) is a phenyl group.

15. The curable silicone composition according to claim 14, wherein component (B) is present in an amount such that the silicon-bonded hydrogen atoms in component (B) is from 0.5 to 5 moles per 1 mole of the alkenyl groups in component (A).

16. The curable silicone composition according to claim 15, wherein a content of aryl groups in component (C) is at least 10 mol % based on a total of silicon-bonded organic groups.

* * * * *